(12) United States Patent
Arlt

(10) Patent No.: US 8,791,305 B2
(45) Date of Patent: Jul. 29, 2014

(54) LIGANDS AND CATALYST SYSTEMS FOR HYDROFORMYLATION PROCESSES

(75) Inventor: Dieter Arlt, Rintein (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

(21) Appl. No.: 14/122,594

(22) PCT Filed: May 25, 2012

(86) PCT No.: PCT/EP2012/059850
§ 371 (c)(1),
(2), (4) Date: Jan. 3, 2014

(87) PCT Pub. No.: WO2012/163837
PCT Pub. Date: Dec. 6, 2012

(65) Prior Publication Data
US 2014/0114090 A1    Apr. 24, 2014

(30) Foreign Application Priority Data

May 27, 2011   (DE) .......................... 10 2011 102 666
Aug. 16, 2011   (DE) .......................... 10 2011 110 621

(51) Int. Cl.
C07C 45/00    (2006.01)
C07C 27/04    (2006.01)
B01J 31/00    (2006.01)
B01J 27/185   (2006.01)

(52) U.S. Cl.
USPC ............ 568/454; 568/852; 502/166; 502/213

(58) Field of Classification Search
USPC .......................... 568/454, 852; 502/166, 213
See application file for complete search history.

(56) References Cited

U.S. PATENT DOCUMENTS

| | | | |
|---|---|---|---|
| 4,064,145 A | 12/1977 | Taylor | |
| 4,215,077 A | 7/1980 | Matsumoto et al. | |
| 4,238,419 A | 12/1980 | Matsumoto et al. | |
| 4,678,857 A | 7/1987 | Dureanleau et al. | |
| 5,290,743 A | 3/1994 | Chang | |
| 7,279,606 B1 | 10/2007 | White | |
| 7,294,602 B1 | 11/2007 | White | |
| 7,655,821 B1 | 2/2010 | White et al. | |

FOREIGN PATENT DOCUMENTS

| | | |
|---|---|---|
| WO | 2008/121194 A1 | 10/2008 |
| WO | 2010/132087 A1 | 11/2010 |
| WO | 2012/163831 A1 | 12/2012 |

OTHER PUBLICATIONS

Boogaerts, et al. (2010) "High chemo and regioselective formation of alcohols from the hydrocarbonylation of alkenes using cooperative ligand effects" Chem. Commun., 46, 2194-2196.
International Search Report for Application No. PCT/EP2012/059850 mailed Aug. 3, 2012 (in English).

*Primary Examiner* — Jafar Parsa
(74) *Attorney, Agent, or Firm* — Smith, Gambrell & Russell, LLP.

(57) ABSTRACT

The present invention relates to ligands and catalyst systems for the hydroformylation of short and long chain olefins, preferably for the hydroformylation of allyl alcohol producing 4-hydroxybutyraldehyde. The ligands disclosed herein are all-trans phosphinomethyl-cyclobutane ligands, such as, for example, all-trans-1,2,3,4-tetra[bis-(3,5-xylyl)phosphinomethyl]-cyclobutane. The catalyst systems comprise these all-trans phosphinomethyl-cyclobutane ligands in combination with an organometallic rhodium complex such as, e.g., (acetylacetonato)-dicarbonyl-rhodium (I). The ligands and catalyst systems of the present invention may be employed in the hydroformylation of olefins, in particular in the hydroformylation of allylalcohol, and provide improved selectivity and high reaction yields. wherein $R^1$ is alkyl, preferably methyl, ethyl or propyl, $R^2$ is H or an alkoxy group, $R^3$ and $R^4$, independently of one another, $CH_2OR^1$, $CH_2O$-aralkyl, $CH_2OH,CH_2$—$[P(3,5-R^1,R^1-4-R^2-phenyl)_2]$ or $CH_2O$—$(CH_2$—$CH_2$—$O)_m$—H (with m being an integer between 1 and 1.000).

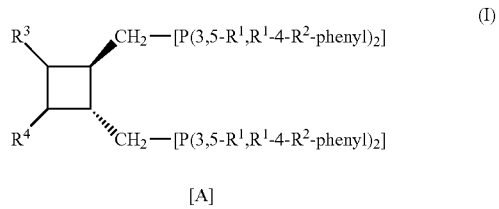

[A]

13 Claims, No Drawings

LIGANDS AND CATALYST SYSTEMS FOR HYDROFORMYLATION PROCESSES

The present invention relates to novel ligands and catalyst systems for hydroformylation processes of short and long chain olefins, for example for the hydroformylation of allyl alcohol to produce 4-hydroxybutyraldehyde. The preparation of these ligands and catalysts as well as their use in hydroformylation reactions is disclosed.

BACKGROUND OF THE INVENTION

The hydroformylation of allyl alcohol is known and is utilized industrially (see e.g. U.S. Pat. No. 4,064,145; U.S. Pat. No. 4,215,077; U.S. Pat. No. 4,238,419; U.S. Pat. No. 4,678,857; U.S. Pat. No. 5,290,743). Allyl alcohol is reacted in these processes with $CO/H_2$ gas mixtures, giving 4-hydroxybutyraldehyde (HBA). Following distillative removal of undesired by-products, HBA is hydrogenated in a known manner to give 1,4-butanediol (BDO).

Recently, rhodium complexes together with diphosphine ligands such as DIOP (2,3-O-isopropylidene-2,3-dihydroxy-1,4-bis-[bis(3,5-dimethylphenyl)phosphino]-butane) have been employed for hydroformylation reactions.

A general disadvantage of this mode of production is the formation of undesired by-products. In particular, as well as the desired linear product, the isomeric branched product 3-hydroxy-2-methylpropionaldehyde (HMPA) and other $C_3$ by-products such as n-propanol and propionaldehyde are formed. This adversely affects the economic viability of the process.

The present invention provides phosphine ligands which are based on a cyclobutane ligand containing at least two trans-coordinated (3,5-dialkyl-phenyl)phosphinomethyl groups. In a further aspect, the present invention provides catalyst systems which are formed from a rhodium complex and said cyclobutane ligand comprising at least two trans-coordinated (3,5-dialkylphenyl)-phosphinomethyl groups.

The ligands and catalyst systems of the present invention allow more favorable HBA:HMPA-proportions to be achieved in the hydroformylation of allyl alcohole, and thus provide improved selectivity and high reaction yields.

DETAILED DESCRIPTION OF THE INVENTION

Generally, the phosphine ligands disclosed in this invention can be defined as phosphinomethyl-cyclobutanes having the formula [A]

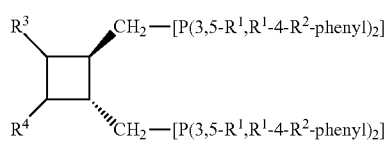

[A]

wherein
$R^1$ is alkyl, preferably methyl, ethyl or propyl
$R^2$ is H or an alkoxy group,
$R^3$ and $R^4$, independently of one another, are $CH_2OR^1$, $CH_2O$-aralkyl, $CH_2OH$, $CH_2$—[P(3,5-$R^1$,$R^1$-4-$R^2$-phenyl)$_2$] or $CH_2O$—($CH_2$—$CH_2$—O)$_m$—H (with m being an integer between 1 and 1,000)

Preferably, [A] is an all-trans-phosphinomethyl-cyclobutane derivative and the phosphine ligands are all-trans-phosphinomethyl-cyclobutanes of formula [A],
wherein
$R^1$ is methyl, ethyl or propyl,
$R^2$ is H,
$R^3$ and $R^4$, independently of one another, are $CH_2OR^1$, $CH_2OH$ or $CH_2$—[P(3,5-$R^1$,$R^1$-4-$R^2$-phenyl)$_2$]

Further preferred are the ligands [A] having the composition
all-trans-1,2,3,4-tetra[bis-(3,5-xylyl)phosphinomethyl]-cyclobutane and
all-trans-1,2,3-tris[bis-(3,5-xylyl)phosphinomethyl]-4-(methoxymethyl)-cyclobutane,
all-trans-1,2,3-tris[bis-(3,5-xylyl)phosphinomethyl]-4-(hydroxymethyl)-cyclobutane,
all-trans-1,2,3-tris[bis-(3,5-xylyl)phosphinomethyl]-4-[$CH_2$—(O—$CH_2$—$CH_2$—O)$_m$H]-cyclobutane (with m being an integer between 1 and 1.000). The ligands may be used as individual compounds or in the form of mixtures or ligand combinations.

In a still further preferred embodiment, the phosphine ligands are all-trans-phosphinomethyl-cyclobutanes of formula [A], wherein
$R^1$ is methyl, ethyl or propyl,
$R^2$ is H,
$R^3$ and $R^4$ are $CH_2$—[P(3,5-$R^1$,$R^1$-4-$R^2$-phenyl)$_2$].

In addition to the phosphine ligands of formula [A], the catalysts and catalyst systems of the present invention also comprise a rhodium complex. Examples for suitable rhodium complexes include (acetylacetonato)-dicarbonyl-rhodium(I) [Rh(CO)$_2$acac], tris-(triphenylphosphine)-rhodium-carbonyl-hydride[Rh(PPh)$_3$(CO)H], (triphenylphosphine)-carbonyl-rhodium(I)-acetylacetonate[Rh(CO)(PPh$_3$)acac], cyclooctadienylrhodium(I)-chloride-dimer[(COD)RhCl]$_2$ and Rh(III)-ethylhexanoate. The preferred Rh complex is (acetylacetonato)-dicarbonyl-rhodium(I).

In the practice of this invention, the rhodium complex is employed in such an amount that the Rh concentration within the reaction mixture ranges from about 0.05 to 100 mg Rh/l, preferably 0.1 to 25 mg Rh/l. Lower Rh concentrations may reduce the reaction rate and yield.

The molar ratio of the phosphinomethyl-cyclobutane ligand:rhodium complex is generally in the range of 0.5:1 to 10:1, preferably in the range of 1:1 to 5:1. Usually, the phosphinomethyl-cyclobutane ligand and the rhodium complex are added to the reaction mixture before the olefine compound (e.g. allyl alcohol) is added.

Usually, the hydroformylation of olefinic compounds such as allyl alcohol is carried out in homogeneous phase. Polar and/or non-polar solvents may be employed. Polar solvents which may be used are, for example, ethanol, n-propanol, iso-propanol n-butanol, isobutanol. Suitable non-polar solvents are aromatic or aliphatic hydrocarbons, such as benzene, toluene or xylene. Generally, the solvents used in the process should be able to solubilize the rhodium complex employed.

Basically, the ligands and catalyst systems of the present invention can be used in hydroformylation reactions of short and long-chain olefins. As examples for short-chain olefins, there may be mentioned ethylene, propylene, 1-butene, isobutene, 1-pentene and the like.

Preferably, the ligands and catalyst systems of the present invention are employed in the hydroformylation of allylalcohol. In this specific application, the ligands and catalyst systems allow more favorable HBA:HMPA-proportions to be achieved, and thus provide improved selectivity and high reaction yields.

An additional aspect of the invention is the use of the catalyst systems containing the ligands of the formula [A] which permit different embodiments of the hydroformylation process.

Novel hydrophilic catalyst systems comprising the ligands of the formula [A] with polyether groups (such as $CH_2O$—$(CH_2$—$CH_2$—$O)_m$—H with m being an integer between 1 and 1,000) may be used in membrane reactors and thus allow the process products to be separated off continuously after the hydroformylation.

The hydroformylation takes place under reaction conditions known in the prior art, typically in a temperature range from 20 to 120° C. and in a pressure range from 2-20 bar. The optimum performance is ascertained by appropriate preliminary experiments depending on the existing equipment.

The molar ratio of the synthesis gas mixture (CO/hydrogen) employed is $CO:H_2\sim1:1$, but it can vary considerably depending on the embodiment.

The reaction time is in the range of 0.5 to 4 hours. At the start of the reaction, the allyl alcohol concentration is 5 to 50%, preferably 10 to 25%, based on the solvent or solvent mixture.

After the reaction, HBA, HMPA and other by-products are separated off from the catalyst, preferably by extraction with water.

In a later step, HBA (and HMPA) are hydrogenated to give the corresponding dihydroxy compounds, and fractional distillation of the crude product gives the desired 1,4-butanediol (BDO) in pure form.

The examples below further illustrate the invention:

Example 1

Preparation of the Novel Ligands According to the Invention a) Preparation of all-trans-1,2-bis[bis-(3,5-xylyl)phosphinomethyl]-3,4-bis(trityloxymethyl)-cyclobutane 88 mg (0.5 mmol) of all-trans-1,2,3,4-tetra(hydroxymethyl)cyclobutane were dissolved in 3 ml of anhydrous pyridine and, at 0° C., 251 mg (0.9 mmol) of trityl chloride were added with intense stirring. The reaction mixture was kept at 0° C. overnight with stirring. Then, it was added to 10 ml of water and extracted with ethyl acetate (3×5 ml), then dried with $MgSO_4$ and evaporated to dryness in a rotary evaporator.

The crude product was separated off by chromatography (silica gel). (Eluent:ethyl acetate:hexane 1:3→2:3→ethyl acetate:methanol 95:5).

The main product obtained was 114 mg (34% of theory) of all-trans-1,2-bis(hydroxymethyl)-3,4-bis(trityloxymethyl) cyclobutane.

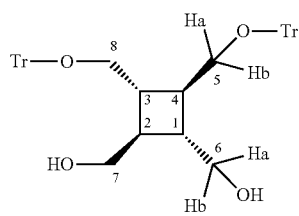

$^1$H-NMR (550 MHz, $CDCl_3$): 7.15-7.4
(m, 15H, Ar); 3.86 (m, 2H, H-6a, H-7a);
3.63 (m, 2H, H-6b, H-7b);
3.18 (m 2H, H-5a, H-8a);
2.98 (m, 2H, H-5b, H-8b); 1.84
(m, 4H, H-1, H-2, H-3 and H-4);
$^{13}$C-NMR ($CDCl_3$): 143.95;
128.60; 127.79; 126.98; 86.84;
66.24; 65.71; 43.68; 39.06.

In a manner known in the art, the two OH-groups of this compound are tosylated and reacted with $LiP(3,5-xylyl)_2$ to yield all-trans-1,2-bis[bis-(3,5-xylyl)phosphinomethyl]-3,4-bis(trityloxymethyl)-cyclobutane. In further steps (optional), the two trityl groups may be removed or may be exchanged by alkyl or alkoxy groups.

b) Preparation of all-trans-1,2,3,4-tetra[bis-(3,5-xylyl)phosphinomethyl]-cyclobutane The starting compound all-trans-1,2,3,4-tetra(hydroxymethyl)-cyclobutane is tosylated in a matter known per se by reaction with 4 equivalents of tosylchloride (p-toluolsulfonic acid chloride) in the presence of a base in a chlorinated hydrocarbon solvent (e.g. dichloromethane) in the presence of a base (e. pyridine). The tetra-tosylated compound is isolated and the solvent is removed in vacuo.

In the next step, the tetra-tosylated compound is reacted with 4 equivalents of $LiP(3,5-xylyl)_2$ in a dry ether solvent (e.g. EG/DME mixture) to yield the all-trans tetraphosphinomethyl-cyclobutane ligand.

Example 2

Hydroformylation Corresponding to the Process According to the Invention

In 4 ml of dried and degassed tert-butyl methyl ether, 16 mmol of all-trans-1,2,3,4-tetra[bis-(3,5-xylyl)phosphinomethyl]-cyclobutane are reacted under argon with $[Rh(CO)_2(acac)]$(8 mmol).

The resulting solution is injected into an autoclave under argon and flushed with a $CO:H_2$-1:1 mixture. Via a side arm, a solution of 1 ml of allyl alcohol in 15 ml of ethanol is then added and the reaction is carried out at a pressure of 40 bar and a temperature of 120° C. This gives 97% of theory of HBA+HMPA in a ratio of ca. 14:1 (selectivity HBA/HMPA=93.3%).

Example 3

Comparative Hydroformylation Experiments

These experiments are conducted in a 60 ml autoclave under argon at a temperature of 65° C. and a pressure of p=20 bar of synthesis gas ($CO/H_2$=1:1). The reaction time is 120 mins.

A solution of the respective phosphine ligand (2 equivalents or 8.6×10⁻⁵ mole) in 15 grams of dry degassed toluene is added to [Rh(CO)₂acac] (1 equivalent or 4.3×10⁻⁵ mole) in the autoclave. The autoclave is pressurized at 20 bar, then heated to 65° C. and the allyl alcohol (3.5 ml) is injected. After 120 mins, the gas uptake is completed and the autoclave is cooled. The resulting solution is analyzed by gas chromatography to determine the reaction products 4-hydroxyl-butyraldehyde (HBA) and 3-hydroxy-2-methylpropionaldehyde (HMPA). The selectivity is determined by the ratio of the product peak area (HBA) vs. the side product peak area (HMPA). The results are summarized in Table 1:

TABLE 1

Comparative hydroformylation experiments

| Phosphine ligand | Selectivity HBA/HMPA |
| --- | --- |
| All-trans-1,2,3,4-tetra[bis-(3,5-xylyl)phosphinomethyl]-cyclobutane (this invention) | 98% |
| Trans-(1,2)-bis[bis-(3,5-dimethylphenyl)-Phosphinomethyl]-cyclobutane (ref to U.S. Pat. No. 7,655,821B1) | 96% |
| 2,3-O-isopropylidene-2,3-dihydroxy-1,4-bis-[bis(3,5-dimethylphenyl)phosphino]butane (DIOP) | 96% |

As can be seen from Table 1, the ligands and catalytic systems of the present invention allow more favorable HBA:HMPA-proportions to be achieved in the hydroformylation of allyl alcohole, and thus provide improved selectivity and high reaction yields.

The invention claimed is:

1. A phosphinomethyl-cyclobutane ligand having the formula [A]

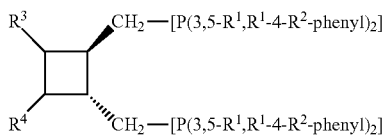

[A]

wherein
R¹ is alkyl,
R² is H or an alkoxy group,
R³ and R⁴, independently of one another, $CH_2OR^1$, $CH_2O$-aralkyl, $CH_2OH$, $CH_2$—[P(3,5-R¹,R¹-4-R²-phenyl)₂] or $CH_2O$—$(CH_2$—$CH_2$—$O)_m$—H, with m being an integer between 1 and 1,000.

2. The phosphinomethyl-cyclobutane ligand according to claim 1, wherein
R¹ is methyl, ethyl or propyl,
R² is H,
R³ and R⁴ are $CH_2$—[P(3,5-R¹,R¹-4-R²-phenyl)₂].

3. The phosphinomethyl-cyclobutane ligand according to claim 1, selected from the group consisting of all-trans-1,2,3,4-tetra[bis-(3,5-xylyl)phosphinomethyl]-cyclobutane, all-trans-1,2,3-tris[bis-(3,5-xylyl)phosphinomethyl]-4-(methoxymethyl)-cyclobutane, all-trans-1,2,3-tris[bis-(3,5-xylyl)phosphinomethyl]-4-(hydroxymethyl)-cyclobutane, all-trans-1,2-bis[bis-(3,5-xylyl)phosphinomethyl]-3,4-bis(trityloxymethyl)-cyclobutane and all-trans-1,2,3-tris[bis-(3,5-xylyl)phosphinomethyl]-4-[CH₂—(O—CH₂—CH₂—O)ₘH]-cyclobutane, with m being an integer between 1 and 1,000, and mixtures and combinations thereof.

4. A catalyst system for the hydroformylation of olefins, comprising a rhodium complex and a phosphinomethyl-cyclobutane ligand having the formula [A]

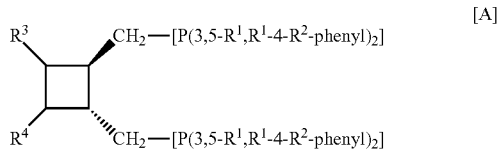

[A]

wherein
R¹ is alkyl,
R² is H or an alkoxy group,
R³ and R⁴, independently of one another, $CH_2OR^1$, $CH_2O$-aralkyl, $CH_2OH$, $CH_2$—[P(3,5-R¹,R¹-4-R²-phenyl)₂] or $CH_2O$—$(CH_2$—$CH_2$—$O)_m$—H, with m being an integer between 1 and 1,000.

5. The catalyst system according to claim 4, wherein
R¹ is methyl, ethyl or propyl,
R² is H,
R³ and R⁴ are $CH_2$—[P(3,5-R¹,R¹-4-R²-phenyl)₂].

6. The catalyst system according to claim 4, wherein the rhodium complex is selected from the group consisting of (acetylacetonato)-dicarbonyl-rhodium(I) [Rh(CO)₂acac], tris-(triphenylphosphine)-rhodium-carbonyl-hydride[Rh(PPh₃)₃(CO)H], (triphenylphosphine)-carbonyl-rhodium(I)-acetylacetonate[Rh(CO)(PPh₃)acac], cyclooctadienyl-rhodium(I)-chloride-dimer[(COD)RhCl]₂, Rh(III)-ethyl hexanoate and mixtures and combinations thereof.

7. The catalyst system according to claim 4, wherein the rhodium complex is (acetylacetonato)-dicarbonyl-rhodium (I) [Rh(CO)₂acac].

8. The catalyst system according to claim 4, wherein the phosphinomethyl-cyclobutane ligand is selected from the group consisting of all-trans-1,2,3,4-tetra[bis-(3,5-xylyl)phosphinomethyl]-cyclobutane, all-trans-1,2,3-tris[bis-(3,5-xylyl)phosphinomethyl]-4-(methoxymethyl)-cyclobutane, all-trans-1,2,3-tris [bis-(3,5-xylyl)phosphinomethyl]-4-(hydroxymethyl)-cyclobutane, all-trans-1,2-bis [bis-(3,5-xylyl)phosphinomethyl]-3,4-bis(trityloxymethyl)-cyclobutane and all-trans-1,2,3-tris[bis-(3,5-xylyl)phosphinomethyl]-4-[CH2-(O—CH2-CH2-O)mH]-cyclobutane, with m being an integer between 1 and 1,000, and mixtures and combinations thereof.

9. The catalyst system according to claim 4, wherein the molar ratio phosphinomethyl-cyclobutane ligand:rhodium complex is in the range of 0.5:1 to 10:1.

10. A process for the hydroformylation of allylalcohol comprising utilizing the phosphinomethyl-cyclobutane ligands according to claim 1.

11. A process for the hydroformylation of allylalcohol comprising utilizing catalyst system according to claim 4.

12. The phosphinomethyl-cyclobutane ligand according to claim 1, wherein R¹ is methyl, ethyl or propyl.

13. The catalyst system according to claim 4, wherein R¹ is methyl, ethyl or propyl.

* * * * *